(12) United States Patent
Burkett et al.

(10) Patent No.: US 10,350,389 B2
(45) Date of Patent: Jul. 16, 2019

(54) INTRAVASCULAR DEVICES, SYSTEMS, AND METHODS HAVING A RADIOPAQUE PATTERNED FLEXIBLE TIP

(71) Applicant: Volcano Corporation, San Diego, CA (US)

(72) Inventors: David Burkett, Temecula, CA (US); Ramiro Reyes, Oceanside, CA (US)

(73) Assignee: VOLCANO CORPORATION, San Diego, CA (US)

( * ) Notice: Subject to any disclaimer, the term of this patent is extended or adjusted under 35 U.S.C. 154(b) by 0 days.

(21) Appl. No.: 14/930,105

(22) Filed: Nov. 2, 2015

(65) Prior Publication Data

US 2016/0121085 A1  May 5, 2016

Related U.S. Application Data (60) Provisional application No. 62/074,320, filed on Nov. 3, 2014.

(51) Int. Cl.
  *A61B 5/00* (2006.01)
  *A61B 5/026* (2006.01)
  (Continued)

(52) U.S. Cl.
  CPC .............. *A61M 25/09* (2013.01); *A61B 5/026* (2013.01); *A61B 5/0215* (2013.01);
  (Continued)

(58) Field of Classification Search
  CPC ........ A61M 25/09; A61M 2025/09058; A61M 2025/09066; A61M 2025/09083;
  (Continued)

(56) References Cited

U.S. PATENT DOCUMENTS 5,125,137 A    6/1992   Corl
5,715,827 A *  2/1998   Corl ..................... A61B 5/0215
                                                        600/486

(Continued)

FOREIGN PATENT DOCUMENTS

WO    WO2011/092190       8/2011
WO    WO2015/117066 A1    8/2015

OTHER PUBLICATIONS

International Search Report and Written Opinion of the International Searching Authority for PCT Patent Application No. PCT/US2015/014076, dated May 27, 2015, 12 Pages.

*Primary Examiner* — Devin B Henson (57) ABSTRACT

Intravascular devices, systems, and methods are disclosed. In some instances, the intravascular device is a guide wire with distal tip element having a radiopaque marker pattern. For example, in some implementations a sensing guide wire includes a flexible elongate member; a sensing element coupled to the flexible elongate member; a flexible tip element coupled to and extending distally from the sensing element, the flexible tip element having a first radiopaque section, a second radiopaque section, and a non-radiopaque section positioned between the first and second radiopaque sections. Methods of making, manufacturing, and/or assembling such intravascular devices and associated systems are also provided.

17 Claims, 5 Drawing Sheets

(51) Int. Cl.
*A61M 25/09* (2006.01)
*A61B 5/0215* (2006.01)

(52) U.S. Cl.
CPC ........ *A61B 5/6851* (2013.01); *A61B 2562/12* (2013.01); *A61M 2025/09166* (2013.01)

(58) Field of Classification Search
CPC ......... A61M 2025/09108; A61M 2025/09166; A61B 5/6851
See application file for complete search history.

(56) References Cited

U.S. PATENT DOCUMENTS

| | | | |
|---|---|---|---|
| 5,873,835 A | 2/1999 | Hastings | |
| 6,090,052 A | 7/2000 | Akerfeldt et al. | |
| 6,106,476 A | 8/2000 | Corl | |
| 6,500,147 B2 * | 12/2002 | Omaleki | A61M 25/09 604/103.09 |
| 6,551,250 B2 | 4/2003 | Khalil | |
| 6,620,114 B2 * | 9/2003 | Vrba | A61M 25/09 33/511 |
| 7,722,552 B2 * | 5/2010 | Aimi | A61M 25/09 600/585 |
| 2003/0028128 A1 | 2/2003 | Tenerz | |
| 2004/0210163 A1 * | 10/2004 | Osawa | A61M 25/09 600/585 |
| 2005/0054952 A1 * | 3/2005 | Eskuri | A61M 25/09 600/585 |
| 2006/0074318 A1 | 4/2006 | Ahmed et al. | |
| 2011/0301501 A1 * | 12/2011 | Tsunezumi | A61M 25/09 600/585 |
| 2014/0005543 A1 | 1/2014 | Burkett | |
| 2014/0180141 A1 | 6/2014 | Millett | |
| 2014/0187874 A1 | 7/2014 | Burkett | |
| 2014/0187980 A1 | 7/2014 | Burkett | |
| 2014/0187984 A1 | 7/2014 | Burkett | |
| 2015/0217090 A1 | 8/2015 | Burkett | |

* cited by examiner

INTRAVASCULAR DEVICES, SYSTEMS, AND METHODS HAVING A RADIOPAQUE PATTERNED FLEXIBLE TIP

CROSS REFERENCE TO RELATED APPLICATIONS

The present application claims priority to and the benefit of the U.S. Provisional Patent Application No. 62/074,320, filed Nov. 3, 2014, which is hereby incorporated by reference in its entirety.

TECHNICAL FIELD

The present disclosure relates to intravascular devices, systems, and methods. In some embodiments, the intravascular devices are guide wires that include a distal tip element having a radiopaque marker pattern.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guide wires are utilized to measure the pressure within the blood vessel, visualize the inner lumen of the blood vessel, and/or otherwise obtain data related to the blood vessel. To date, guide wires containing pressure sensors, imaging elements, and/or other electronic, optical, or electro-optical components have suffered from reduced performance characteristics compared to standard guide wires that do not contain such components. For example, the handling performance of previous guide wires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guide wire.

Further, a problem with existing pressure and flow guide wires is that the coil(s) defining the distal tip of the device can be fragile and prone to unwanted bending or kinking. In that regard, the small diameter and high flexibility of the coil(s) limits the structural integrity that can be provided. Further, in some implementations the tip coil is formed of a radiopaque material to allow the device to be identified during a procedure using fluoroscopy. However, a solid radiopaque tip coil provides little to no indication of the relative orientation of the device and, therefore, can make it difficult for the medical personnel and/or other medical processing systems to correlate the current location of the device with other information or images of the vessel.

Accordingly, there remains a need for intravascular devices, systems, and methods that include one or more electronic, optical, or electro-optical components and have improved visualization characteristics under fluoroscopy.

SUMMARY

The present disclosure is directed to intravascular devices, systems, and methods that include a guide wire having a distal tip element having a radiopaque marker pattern.

In some implementations, a sensing guide wire is provided that includes a flexible elongate member; a sensing element coupled to the flexible elongate member; a flexible tip element coupled to and extending distally from the sensing element, the flexible tip element having a first radiopaque section, a second radiopaque section, and a non-radiopaque section positioned between the first and second radiopaque sections. The sensing element is a pressure sensor in some instances. The guide wire can also include a flow sensor coupled to a distal end of the flexible tip element. The first radiopaque section can be positioned adjacent a sensor housing in which the sensing element is disposed. The first and second radiopaque sections can each be defined by a coil formed of a radiopaque material, such platinum, tungsten, gold, or other suitable material. Also, the non-radiopaque section can be defined by a coil formed of a non-radiopaque material, such as stainless steel or other suitable material. Each of the first and second radiopaque sections and the non-radiopaque section can have equal lengths. In some instances, the first and second radiopaque sections are welded to the non-radiopaque section. The flexible tip element can have an outer diameter of approximately 0.014", 0.018", 0.035", or other size. In some instances, the coils defining the flexible tip element have a pitch of approximately 0.00295" and/or are formed from a wire having an diameter of approximately 0.0026". The flexible tip element has a length of approximately 3 cm in some implementations, with the first and second radiopaque sections each having a length between 2 mm and 6 mm and the non-radiopaque section having a length between 2 mm and 12 mm.

In some implementations, a method of forming a sensing guide wire is provided that includes coupling a sensing element to a distal portion of a flexible elongate member; and coupling a flexible tip element to the sensing element such that the flexible tip element extends distally from the sensing element, the flexible tip element having a first radiopaque section, a second radiopaque section, and a non-radiopaque section positioned between the first and second radiopaque sections.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a flow sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guide wire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm), approximately 0.018" (0.4572 mm), and approximately 0.035" (0.889 mm). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Figure 1:
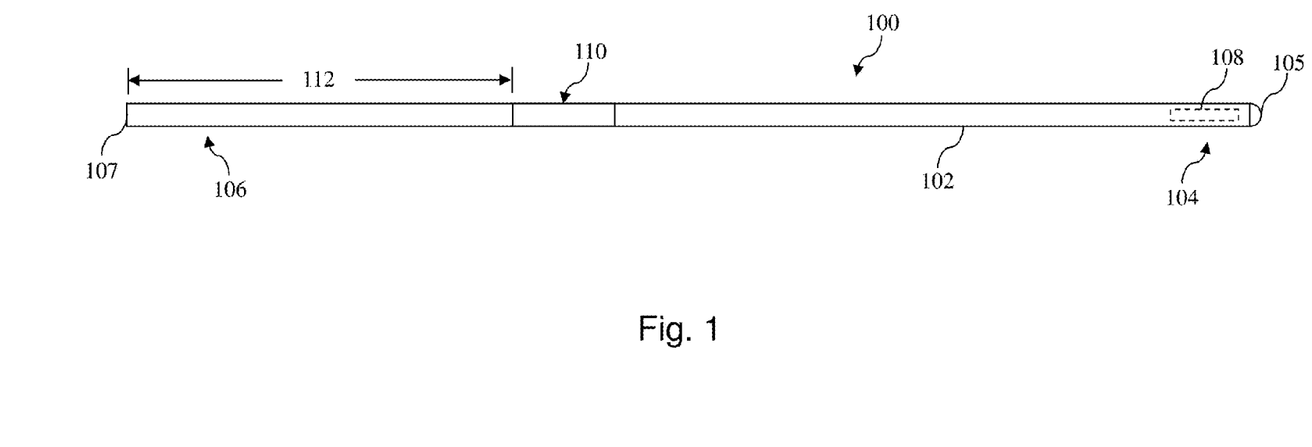
FIG. 1 is a diagrammatic, schematic side view of an intravascular device according to an embodiment of the present disclosure.

Referring now to FIG. 1, shown therein is a portion of an intravascular device 100 according to an embodiment of the present disclosure. In that regard, the intravascular device 100 includes a flexible elongate member 102 having a distal portion 104 adjacent a distal tip 105 and a proximal portion 106 adjacent a proximal end 107. A component 108 is positioned within the distal portion 104 of the flexible elongate member 102 proximal of the distal tip 105. Generally, the component 108 is representative of one or more electronic, optical, or electro-optical components. In that regard, the component 108 is a pressure sensor, a flow sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device. In some instances, the component 108 is positioned less than 10 cm, less than 5, or less than 3 cm from the distal tip 105. In some instances, the component 108 is positioned within a housing of the flexible elongate member 102. In that regard, the housing is a separate component secured to the flexible elongate member 102 in some instances. In other instances, the housing is integrally formed as a part of the flexible elongate member 102.

The intravascular device 100 also includes a connector 110 adjacent the proximal portion 106 of the device. In that regard, the connector 110 is spaced from the proximal end 107 of the flexible elongate member 102 by a distance 112. Generally, the distance 112 is between 0% and 50% of the total length of the flexible elongate member 102. While the total length of the flexible elongate member can be any length, in some embodiments the total length is between about 1300 mm and about 4000 mm, with some specific embodiments have a length of 1400 mm, 1900 mm, and 3000 mm. Accordingly, in some instances the connector 110 is positioned at the proximal end 107. In other instances, the connector 110 is spaced from the proximal end 107. For example, in some instances the connector 110 is spaced from the proximal end 107 between about 0 mm and about 1400 mm. In some specific embodiments, the connector 110 is spaced from the proximal end by a distance of 0 mm, 300 mm, and 1400 mm.

The connector 110 is configured to facilitate communication between the intravascular device 100 and another device. More specifically, in some embodiments the connector 110 is configured to facilitate communication of data obtained by the component 108 to another device, such as a computing device or processor. Accordingly, in some embodiments the connector 110 is an electrical connector. In such instances, the connector 110 provides an electrical connection to one or more electrical conductors that extend along the length of the flexible elongate member 102 and are electrically coupled to the component 108. In some embodiments the electrical conductors are embedded within a core of the flexible elongate member. In other embodiments, the connector 110 is an optical connector. In such instances, the connector 110 provides an optical connection to one or more optical communication pathways (e.g., fiber optic cable) that extend along the length of the flexible elongate member 102 and are optically coupled to the component 108. Similarly, in some embodiments the optical fibers are embedded within a core of the flexible elongate member. Further, in some embodiments the connector 110 provides both electrical and optical connections to both electrical conductor(s) and optical communication pathway(s) coupled to the component 108. In that regard, it should be noted that component 108 is comprised of a plurality of elements in some instances. The connector 110 is configured to provide a physical connection to another device, either directly or indirectly. In some instances, the connector 110 is configured to facilitate wireless communication between the intravascular device 100 and another device. Generally, any current or future developed wireless protocol(s) may be utilized. In yet other instances, the connector 110 facilitates both physical and wireless connection to another device.

As noted above, in some instances the connector 110 provides a connection between the component 108 of the intravascular device 100 and an external device. Accordingly, in some embodiments one or more electrical conductors, one or more optical pathways, and/or combinations thereof extend along the length of the flexible elongate member 102 between the connector 110 and the component 108 to facilitate communication between the connector 110 and the component 108. In some instances, at least one of the electrical conductors and/or optical pathways is embedded within the core of the flexible elongate member 102, as described in U.S. Provisional Patent Application No. 61/935,113, filed Feb. 3, 2014, now U.S. patent application Ser. No. 14/611,921 filed Feb. 2, 2015, published as U.S. Patent Application Publication No. 2015/0217090 on Aug. 6, 2015, which is hereby incorporated by reference in its entirety. Generally, any number of electrical conductors, optical pathways, and/or combinations thereof can extend along the length of the flexible elongate member 102 between the connector 110 and the component 108, embedded in the core or not. In some instances, between one and ten electrical conductors and/or optical pathways extend along the length of the flexible elongate member 102 between the connector 110 and the component 108. The number of communication pathways and the number of electrical conductors and optical pathways extending along the length of the flexible elongate member 102 is determined by the desired functionality of the component 108 and the corresponding elements that define component 108 to provide such functionality.

Figure 2:
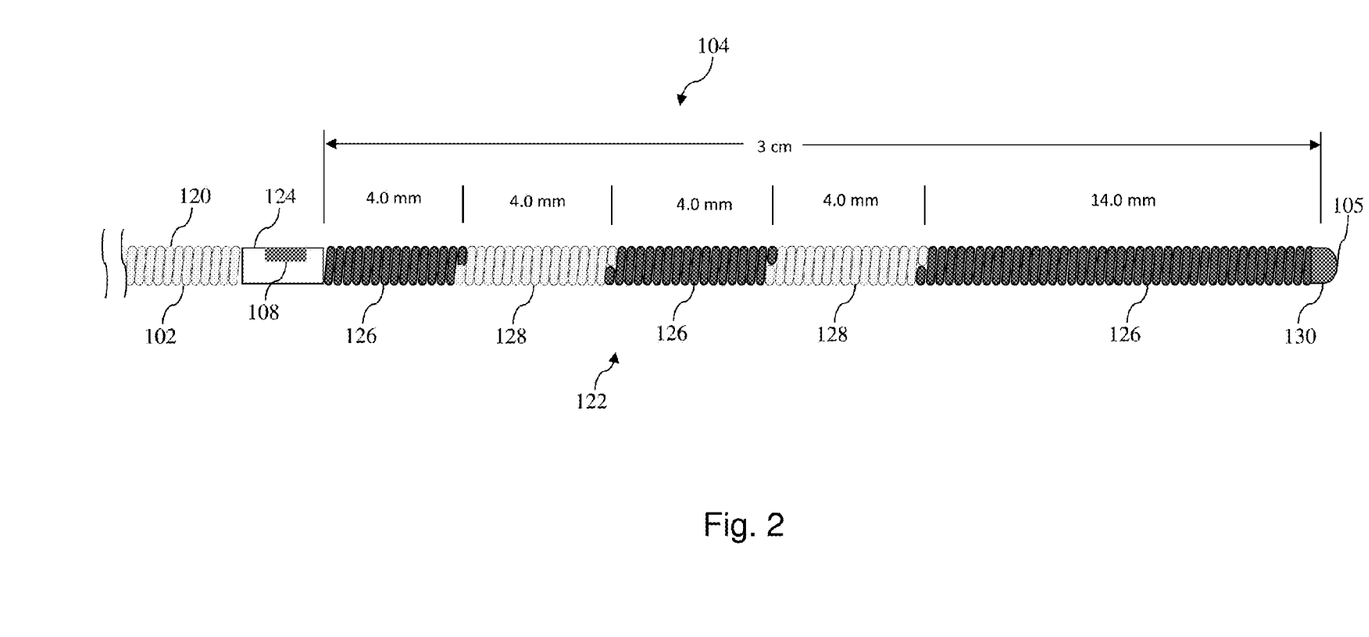
FIG. 2 is a diagrammatic, schematic side view of a distal portion of the intravascular device of FIG. 1 according to an embodiment of the present disclosure.
Figure 3:
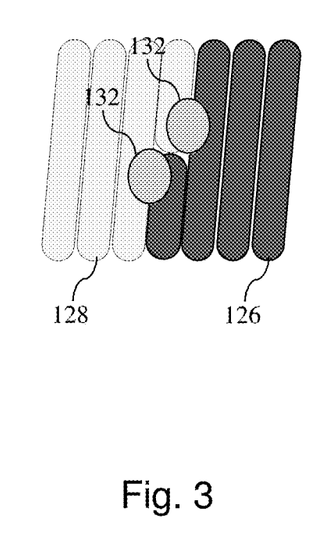
FIG. 3 is a diagrammatic, schematic side view of a connection of adjacent coil components according to an embodiment of the present disclosure.
Figure 4:
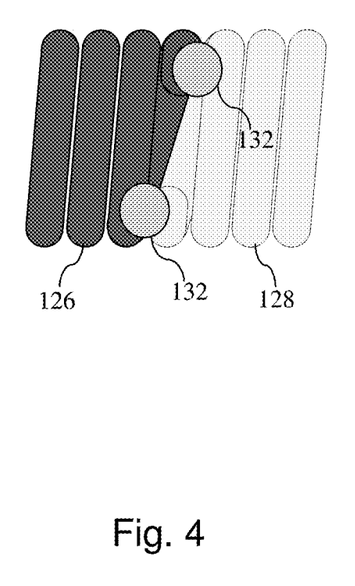
FIG. 4 is a diagrammatic, schematic side view of a connection of adjacent coil components according to another embodiment of the present disclosure.

Referring now to FIGS. 2-4, shown therein are aspects of the intravascular devices of the present disclosure that include a distal tip coil having a radiopaque marker pattern. Referring initially to FIG. 2, shown therein is a diagrammatic, schematic side view of the distal portion 104 of the intravascular device 100 according to an embodiment of the present disclosure. As shown, the distal portion 104 includes a proximal flexible element 120 and a distal flexible element 122 on each side of a housing 124 containing component 108. A proximal core member extends through the proximal flexible element 120. Similarly, a distal core member extends through the distal flexible element 122. In some implementations, the proximal and distal core members are an integral component (i.e., the proximal core member extends through the housing 124 to define core member 128). Generally, the core members are sized, shaped, and/or formed out of particular material(s) to create a desired mechanical performance for the distal portion 104 of the intravascular device 100. In that regard, in some instances the distal core member is coupled to a shaping ribbon. For example, in some particular implementations the distal core member is coupled to a shaping ribbon utilizing a multi-flat transition as described in U.S. Provisional Patent Application No. 62/027,556, filed Jul. 22, 2014, which is hereby incorporated by reference in its entirety.

Figure 5:
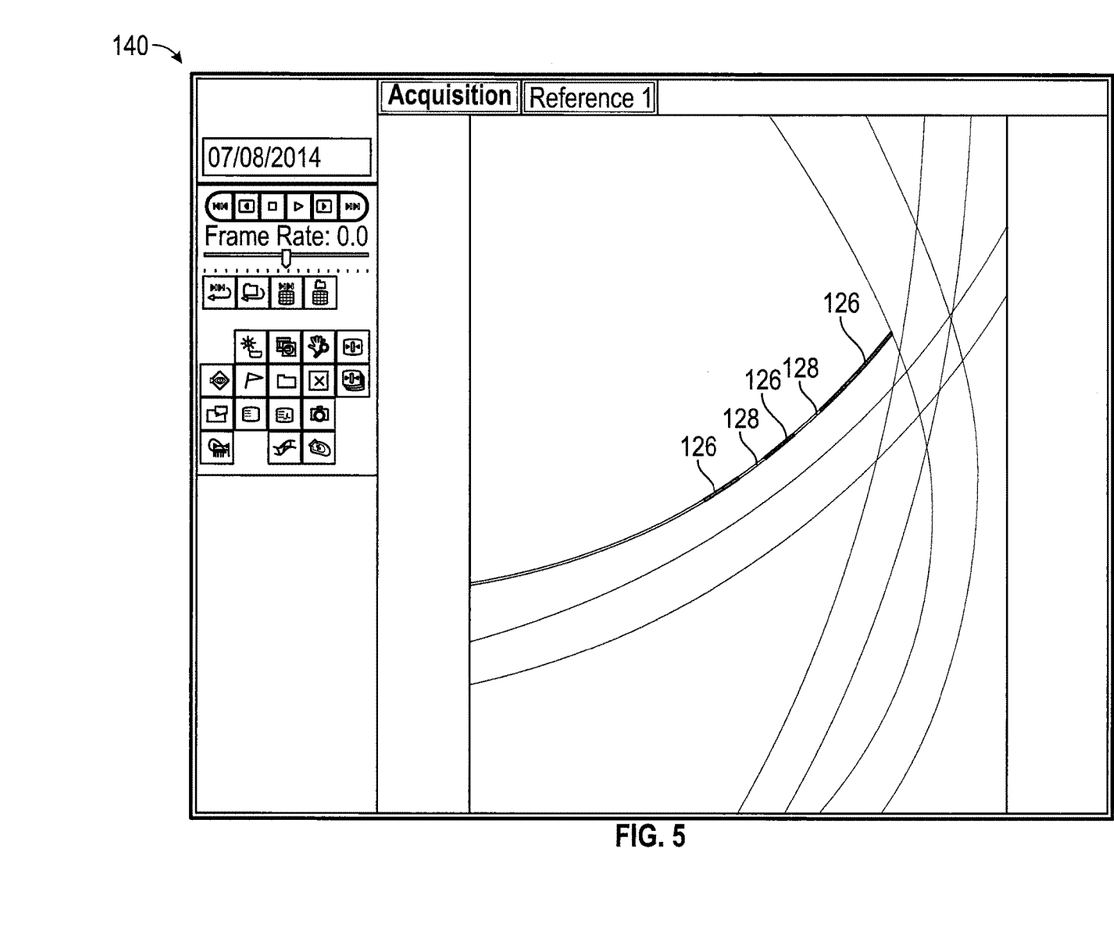
FIG. 5 is a fluoroscopic image of an intravascular device incorporating a radiopaque patterned tip coil according to an embodiment of the present disclosure.

The proximal and distal flexible elements 120, 122 can include any suitable flexible element, including coils (with or without a polymer jacket or other coating), polymer tubes, and/or coil-embedded polymer tubes. In the illustrated embodiment the proximal flexible element 120 is a coil and the distal flexible element 122 is defined by a series of alternating radiopaque coils 126 and non-radiopaque coils 128. In that regard, the non-radiopaque coils 128 are less radiopaque than coils 126 such that the coils 128 are readily distinguishable from the coils 126 under fluoroscopy or other imaging techniques. FIG. 5 illustrates an example of such imaging contrast between the coils 126 and the coils 128. Accordingly, it is understood that the coils 126 and the coils 128 are both radiopaque to varying degrees in order to create such identifiable contrast. As a result, the use of radiopaque and non-radiopaque in the present disclosure is understood to be an indication of the relative radiopacity of the coils 126 and 128 to one another and not necessarily an indication of an absolute measurement of the radiopacity of the coils 126 and 128.

A solder ball 130 or other suitable element is secured to the distal end of the distal flexible element 122. As shown, the solder ball 130 defines the distal tip 105 of the intravascular device 100 with an atraumatic tip suitable for advancement through patient vessels, such as vasculature. In some embodiments, a flow sensor is positioned at the distal tip 105 instead of the solder ball 130.

The distal portion 104 of the intravascular device 100—as well as the proximal portion 106 and the flexible elongate member 102—may be formed using any suitable approach so long as the distal flexible element 122 defines a radiopaque marker pattern in accordance with the present disclosure. Accordingly, in some implementations the intravascular device 100 includes features similar to the distal, intermediate, and/or proximal sections described in one or more of U.S. Pat. Nos. 5,125,137, 5,873,835, 6,106,476, 6,551,250, U.S. patent application Ser. No. 13/931,052, filed Jun. 28, 2013 now published as U.S. Patent Application Publication No. 2014/0005543 on Jan. 2, 2014, U.S. patent application Ser. No. 14/135,117, filed Dec. 19, 2013 now published as U.S. Patent Application Publication No. 2014/0180141 on Jun. 26, 2014, U.S. patent application Ser. No. 14/137,364, filed Dec. 20, 2013 now published as U.S. Patent Application Publication No. 2014/0187980 on Jul. 3, 2014, U.S. patent application Ser. No. 14/139,543, filed Dec. 23, 2013 now published as U.S. Patent Application Publication No. 2014/0187984 on Jul. 3, 2014, U.S. patent application Ser. No. 14/143,304, filed Dec. 30, 2013 now published as U.S. Patent Application Publication No. 2014/0187874 on Jul. 3, 2014, and U.S. Provisional Patent Application No. 61/935,113, filed Feb. 3, 2014, now U.S. patent application Ser. No. 14/611,921 filed Feb. 2, 2015, published as U.S. Patent Application Publication No. 2015/0217090 on Aug. 6, 2015, each of which is hereby incorporated by reference in its entirety.

As shown in FIG. 2, the radiopaque coils 126 form blocks of greater radiopacity or radiodensity with respect to the non-radiopaque coils 128. As such, the radiopaque coils 126 are recognizable in resulting x-ray, fluoroscopy, or other images. In that regard, the alternating pattern of radiopaque coils 126 and non-radiopaque coils 128 can be utilized to determine a relative orientation of the distal flexible element 122 and, thereby, the guide wire 100 within a vessel. To this end, essentially any pattern of radiopaque and non-radiopaque sections can be utilized. Depending on a particular use of the guide wire a different pattern or different size pattern may be desirable. In that regard, it is understood the radiopaque and non-radiopaque sections can have constant spacings, variable spacings, and/or combinations thereof. In some embodiments, each of the radiopaque sections has a length ranging from 1.0 mm to 20.0 mm, from 1.0 mm to 5.0 mm, from 2.0 mm to 4.0 mm, or otherwise. Similarly, each of the non-radiopaque sections can have a length ranging from 1.0 mm to 20.0 mm, from 1.0 mm to 5.0 mm, from 2.0 mm to 4.0 mm, or otherwise. In the illustrated embodiment, the distal flexible element 122 has an overall length of approximately 3 cm that is defined by two 4 mm radiopaque coils 126, two 4 mm non-radiopaque coils 128, and one 14 mm radiopaque coil 126 extending distally from the sensor housing 124 in an alternating pattern, as shown.

In the illustrated embodiment, the radiopaque sections are defined by a stack of radiopaque coils 126 formed by and/or coated with a radiopaque material, while the non-radiopaque section are formed by a stack of non-radiopaque coils 128 formed by a non-radiopaque material (or at least a material less radiopaque than that forming the radiopaque sections). As shown in FIGS. 3 and 4, the radiopaque coils 126 are coupled to the non-radiopaque coils 128 at weld points 132. FIG. 3 shows an implementation where the ends of the coils 126 and 128 are abutted or at least placed in very close proximity and welded in place. FIG. 4 shows an implementation where the ends of the coils 126 and 128 are spaced apart from one another (e.g., by $\frac{1}{16}^{th}$ of a circumference of the coils or more) and welded in place. It is understood that additional welds beyond the particular welds 132 shown in FIGS. 3 and 4 may be used to achieve and maintain a desired coil alignment and/or tensile. In this regard, the separate coils 126 and 128 can be assembled such that they perform similar to a coil wound as a single unit. It is recognized that any pattern of radiopaque and non-radiopaque sections is possible by choosing coils of desired lengths, though more markers require more welds. Further, such an approach provides a very distinct transition between the radiopaque and non-radiopaque sections. Further still, this multi-section approach can be used for the distal tip of the intravascular device that extends distally from a sensing element. In that regard, the need for markers proximal to a sensing element, which are often not desired by physicians, can be eliminated while still providing sufficient marker data to allow co-registration of the location of the intravascular device and, in particular, the sensing element.

Both the radiopaque and non-radiopaque coils 126 and 128 retain the ability to flex. As a result, the radiopaque sections may have greater lengths and resultant visibility in the images than traditional rigid, metallic marker bands without adversely affecting the flexibility of the intravascular device. Thus, the distal flexible element 122 remains capable of curving/bending with the intravascular device 100 as it traverses through tortuous anatomy without causing the inadvertent kinking and/or trauma that can be caused by rigid marker bands.

In the illustrated embodiments, the radiopaque coils 126 and the non-radiopaque coils 128 have substantially similar outer diameters, pitches, and wire diameters. For example, in one implementation of a 0.014" guide wire, the coils 126 and 128 each have an outer diameter of 0.0139" with a 0.00295" pitch using a 0.0026" diameter wire, with the radiopaque coils 126 being formed from a radiopaque material (e.g., platinum/tungsten, etc.) and the non-radiopaque coils 128 being formed from a less radiopaque material (e.g., 304V stainless steel, etc.). The outer diameter, pitch, and/or wire diameter can be selected to achieve desired mechanical properties of the intravascular device. For 0.014" outer diameter intravascular devices, the coils 126 and 128 can have outer diameters between 0.0130" and 0.0145", pitches between 0.0022" and 0.0044", and wire diameters between 0.0020" and 0.0040". For 0.018" outer diameter intravascular devices, the coils 126 and 128 can have outer diameters between 0.0170" and 0.0185", pitches between 0.0022" and 0.0044", and wire diameters between 0.0020" and 0.0040". For 0.035" outer diameter intravascular devices, the coils 126 and 128 can have outer diameters between 0.0260" and 0.0355", pitches between 0.0022" and 0.0066", and wire diameters between 0.0020" and 0.0060". In other embodiments, the radiopaque coils 126 and the non-radiopaque coils 128 may have different outer diameters, pitches, wire diameters, and/or other parameters.

The patterned radiopaque distal flexible element 122 allows co-registration of the location of the intravascular device 100 with other diagnostic techniques, such as external and internal imaging. For example, in some instances the patterned radiopaque distal flexible element 122 is utilized to define a pattern of radiopaque marker elements identifiable by an image processing system. For example, a repeating pattern of radiopaque marker sections with known spacings can be identified using image processing techniques. Benefits of utilizing such an approach include: pressure wires having this patterned tip will be pushed past the lesion of interest and not get in the way of stent markers and can be utilized to identify the exact location of the sensor based on the location of the sensor housing relative to the radiopaque marker pattern. Further, the pattern also provides a method of distinguishing between multiple guidewires and/or catheters positioned within a vessel (e.g., when a sensing guidewwire is being used along with buddy guidewires or catheters). Also, the physician can see the foreshortening effect of the markers (based, for example, on the known marker pattern and how the pattern appears on the current image(s)) to better understand the vessel paths the guidewire is moving through.

Referring now to FIG. 5, shown therein is a fluoroscopic image 140 of an intravascular device incorporating a patterned radiopaque distal flexible element according to an embodiment of the present disclosure. The image 140 shows the distinct contrast between the radiopaque coils 126 and the non-radiopaque coils 128 that allows the location and orientation of the device to be determined by the physician and/or other medical processing equipment.

Guide wires of the present disclosure can be connected to an instrument, such as a computing device (e.g. a laptop, desktop, or tablet computer) or a physiology monitor, that converts the signals received by the sensors into pressure and velocity readings. The instrument can further calculate Coronary Flow Reserve (CFR), Fractional Flow Reserve (FFR), instant wavefree ratio (iFR), or other calculated measurements and provide the readings and calculations to a user via a user interface. In some embodiments, a user interacts with a visual interface to view images associated with the data obtained by the intravascular devices of the present disclosure. Input from a user (e.g., parameters or a selection) are received by a processor in an electronic device. The selection can be rendered into a visible display.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A sensing guide wire, comprising:
a flexible elongate member;
a sensing element coupled to the flexible elongate member; and
a flexible tip element coupled to and extending distally from the sensing element, the flexible tip element having a plurality of radiopaque sections each defined by a coil formed of radiopaque material and a plurality of non-radiopaque sections each defined by a coil formed of non-radiopaque material;
wherein the plurality of radiopaque sections includes only a first radiopaque section, a second radiopaque section, and a third radiopaque section, the third radiopaque section being at a distal end of the flexible tip element;
wherein the plurality of non-radiopaque sections includes only a first non-radiopaque section positioned between the first and second radiopaque sections and a second non-radiopaque section positioned between the second and third radiopaque sections;
wherein the first radiopaque section, the second radiopaque section, the first non-radiopaque section, and the second non-radiopaque section are each shorter than the third radiopaque section;
wherein a distal end of the coil defining the second radiopaque section is welded to a winding of the second non-radiopaque section such that the distal end of the coil defining the second radiopaque section is spaced apart circumferentially from a proximal end of the coil defining the second non-radiopaque section, the second non-radiopaque section being positioned adjacent to the second radiopaque section without windings of the second non-radiopaque section being intertwined with windings of the second radiopaque section; and
wherein a proximal end of the coil defining the second radiopaque section is welded to a winding of the first non-radiopaque section such that the proximal end of the coil defining the second radiopaque section is spaced apart circumferentially from a distal end of the coil defining the first non-radiopaque section, the first non-radiopaque section being positioned adjacent to the second radiopaque section without windings of the first non-radiopaque section being intertwined with windings of the second radiopaque section.

2. The guide wire of claim 1, wherein the sensing element includes at least one of a pressure sensor or a flow sensor.

3. The guide wire of claim 1, wherein the first radiopaque section is adjacent a sensor housing in which the sensing element is disposed.

4. The guide wire of claim 1, wherein the radiopaque material is selected from the group consisting of platinum, tungsten, and gold.

5. The guide wire of claim 1, wherein the non-radiopaque material is selected from the group consisting of stainless steel, MP35N, and ninitol alloys.

6. The guide wire of claim 1, wherein the first and second radiopaque sections are welded to the first non-radiopaque section, and wherein the second and third radiopaque sections are welded to the second non-radiopaque section.

7. The guide wire of claim 1, wherein the flexible tip element has an outer diameter of approximately 0.014", 0.018", or 0.035".

8. The guide wire of claim 7, wherein the coils a pitch of approximately 0.00295".

9. The guide wire of claim 8, wherein the coils are formed from a wire having a diameter of approximately 0.0026".

10. The guide wire of claim 7, wherein the flexible tip element has a length of approximately 3 cm.

11. The guide wire of claim 10, wherein the first and second radiopaque sections each have a length between 2 mm and 20 mm and the first and second non-radiopaque sections have a length between 2 mm and 10 mm.

12. The guide wire of claim 1, wherein the first radiopaque section, the second radiopaque section, the first non-radiopaque section, and the second non-radiopaque section each have a length of 4 mm and the third radiopaque section has a length of 14 mm.

13. The guide wire of claim 1, wherein the distal end of the coil defining the second radiopaque section is spaced apart circumferentially from the proximal end of the coil defining the second non-radiopaque section by at least $\frac{1}{16}^{th}$ of a circumference of the coil defining the second radiopaque section.

14. A method of forming a sensing guide wire, the method comprising:
    coupling a sensing element to a distal portion of a flexible elongate member;
    forming a flexible tip element having a plurality of radiopaque sections each defined by a coil formed of radiopaque material, the plurality of radiopaque sections including only a first radiopaque section, a second radiopaque section, and a third radiopaque section, and the flexible tip element further having a plurality of non-radiopaque sections each defined by a coil formed of non-radiopaque material, the plurality of non-radiopaque sections including only a first non-radiopaque section and a second non-radiopaque section, wherein forming the flexible tip element comprises:
        positioning the third radiopaque section at a distal end of the flexible tip element,
        positioning the first non-radiopaque section between the first and second radiopaque sections,
        positioning the second non-radiopaque section between the second and third radiopaque sections, wherein the first radiopaque section, the second radiopaque section, the first non-radiopaque section, and the second non-radiopaque section are each shorter than the third radiopaque section,
        welding a distal end of the coil defining the second radiopaque section to a winding of the second non-radiopaque section such that the distal end of the coil defining the second radiopaque section is spaced apart circumferentially from a proximal end of the coil defining the second non-radiopaque section, the second non-radiopaque section being positioned adjacent to the second radiopaque section without windings of the second non-radiopaque section being intertwined with windings of the second radiopaque section, and
        welding a proximal end of the coil defining the second radiopaque section to a winding of the first non-radiopaque section such that the proximal end of the coil defining the second radiopaque section is spaced apart circumferentially from a distal end of the coil defining the first non-radiopaque section, the first non-radiopaque section being positioned adjacent to the second radiopaque section without windings of the first non-radiopaque section being intertwined with windings of the second radiopaque section; and
    coupling the flexible tip element to the sensing element such that the flexible tip element extends distally from the sensing element.

15. The method of claim 14, wherein coupling the flexible tip element to the sensing element includes positioning the first radiopaque section adjacent a sensor housing in which the sensing element is disposed.

16. The method of claim 14, further comprising welding the first radiopaque section to the first non-radiopaque section and welding the third radiopaque section to the second non-radiopaque section.

17. The method of claim 14, wherein the flexible tip element has an outer diameter of approximately 0.014", 0.018", or 0.035", wherein the coils have a pitch of approximately 0.00295", and wherein the coils are formed from a wire having a diameter of approximately 0.0026".

* * * * *